United States Patent

Überle

[11] Patent Number: 5,921,930
[45] Date of Patent: Jul. 13, 1999

[54] ARRANGEMENT FOR LOCATING CONCREMENTS IN A PATIENT'S BODY

[75] Inventor: Friedrich Überle, Gilching, Germany

[73] Assignee: Dornier Medizintechnik GmbH, Germany

[21] Appl. No.: 08/773,518

[22] Filed: Dec. 23, 1996

[30] Foreign Application Priority Data

Dec. 21, 1995 [DE] Germany ............................ 195 48 000

[51] Int. Cl.⁶ ............................ A61B 8/00; A61B 17/225
[52] U.S. Cl. ................................................ 600/439; 601/4
[58] Field of Search ..................... 128/660.01, 660.07, 128/661.01, 662.05; 600/437, 439, 443, 447, 459–461

[56] References Cited

U.S. PATENT DOCUMENTS 4,249,539  2/1981  Vilkomerson et al. ............. 600/567 X
5,549,112  8/1996  Cockburn et al. .................. 128/662.05
5,619,999  4/1997  Von Behren et al. .............. 600/459 X Primary Examiner—Francis J. Jaworski
Attorney, Agent, or Firm—Evenson, McKeown, Edwards & Lenahan, P.L.L.C.

[57] ABSTRACT

An arrangement for locating concrements in a patient's body has an acoustic scanning device, a coupling arrangement and an arrangement for producing a marking. The marking arrangement consists of a sensor which is transparent to emitted sound waves and is designed such that, after the expiration of an adjustable delay time, it generates a signal which can be injected as a marking at a predetermined point into the sonic image.

6 Claims, 2 Drawing Sheets

ARRANGEMENT FOR LOCATING CONCREMENTS IN A PATIENT'S BODY

BACKGROUND AND SUMMARY OF THE INVENTION

This invention relates to an arrangement for locating concrements in a patient's body, consisting of a sound source, a coupling arrangement between the sound source and the patient for introducing generated sound waves into the patient's body and an arrangement on the patient's skin for producing a marking in the resulting sound image.

Known devices for applying markings on the skin of a patient are usually coordinated specifically with the particular locating device with which they are mechanically and/or electrically connected. By means of such a marking arrangement, it is possible, after locating a concrement which is to be broken up, to optically mark the skin surface, for example, optically, by means of the locating device. In this manner a therapy head, which generates shock waves for breaking up the concrement, can be aligned at a predetermined position relative to the marking, in order to permit an optimal introduction of the treatment shock waves into the body.

The applicant's German patent document DE-PS 40 03 350 describes an arrangement for positioning an adjustable C-arc X-ray apparatus having an X-ray tube and an image intensifier, with respect to a device for treating patients with extracorporeally generated, focussed shock waves, particularly on a lithotriptor. At least two light sources fastened to the X-ray apparatus generate light beams which cross one another in the isocenter of the C-arc. A reference element, which can be mounted on the treatment unit of the shock wave apparatus, indicates the position of the therapy focus.

In addition, the applicant's German patent document DE-PS 40 33 439 describes a targeting device for X-ray locating in the extracorporeal treatment of patients by means of focussed shock waves, particularly for a lithotriptor. The targeting device consists of a support on or in which X-ray-positive elements are arranged such that they point to the focal spot of the shock wave system. The position of the elements in the x-ray image clearly indicates the position of the focal spot.

As initially mentioned, in the case of the two known devices, the respective marking arrangements are aligned specifically for use with the associated locating arrangements, and cannot be used with other lithotriptors or their locating arrangements.

It is an object of the present invention to provide an arrangement for generating a marking of the location of a therapy focus in a patient which cooperates with any sound source and which permits the injection of the marking at a freely selectible point into the sonic image, so that the location of the focus for the sound therapy apparatus can be shown in the sound image.

This and other objects and advantages are achieved by the marking arrangement according to the invention, in which a sensor array is transparent to the emitted sound waves from the sound source of a given ultrasound image generating apparatus. After the elapse of a set time period following the emission of a sound pulse from the imaging sound source (which period corresponds to the propagation time of a sound pulse to and from a location in space and a direction from the sensor array), the sensor array, which comprises an array of acoustic sensor elements, generates a sound signal that is superimposed as a marking in the form (for example) of a light spot or a graticule at an arbitrarily selectable point on the sonically generated image.

The invention therefore makes it possible to insert a suitable marking, such as a graticule or a light spot, at any point into the sonically generated image, specifically without any electric intervention in the control arrangement of the sound source of the imaging device. Thus, the sound source may be of an arbitrary design, such as for example a conventional medical multi-element scanner or a rotating element scanner.

Other objects, advantages and novel features of the present invention will become apparent from the following detailed description of the invention when considered in conjunction with the accompanying drawings.

DETAILED DESCRIPTION OF THE DRAWINGS

Figure 1:
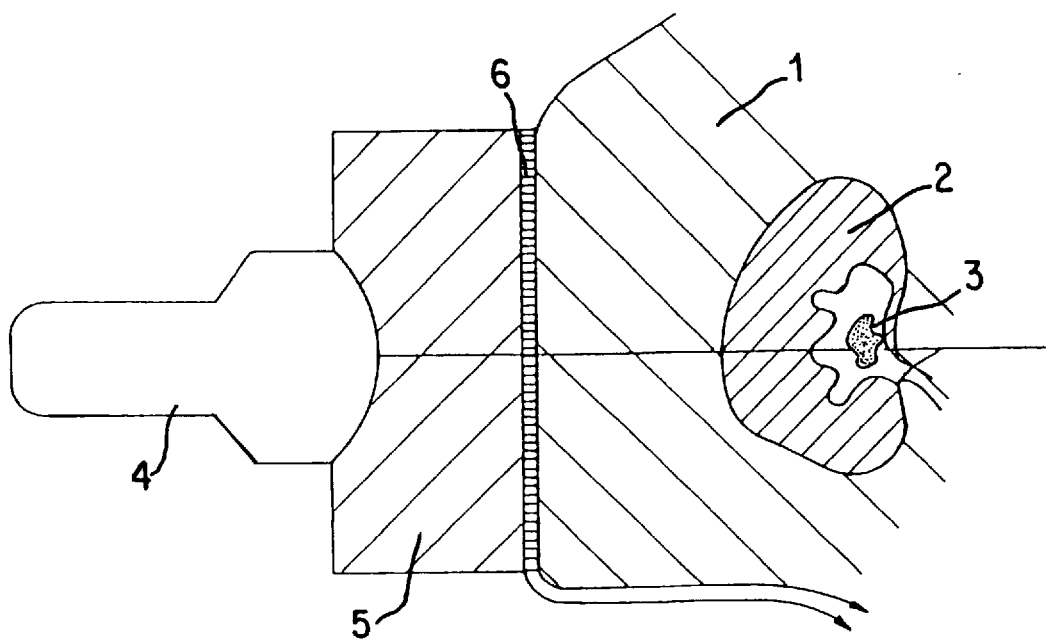
FIG. 1 is a schematic sectional view of a part of the locating arrangement and of the patient.

FIG. 1 is a schematic illustration which shows a part of a patient's body 1 in which a concrement, for example, a stone 3 in a kidney 2, is to be disintegrated by means of shock waves emitted by a therapy head (not shown).

In order to locate the exact position of the concrement 3 in the patient's 1 body, a sound source (scanner) 4, which is aligned with the patient in a conventional manner by means of a coupling arrangement 5, emits directional sound waves according to a predetermined pattern. After finding a concrement 3 by means of the emitted directional sound waves, a sonic image of the concrement can be generated.

According to the invention, a sensor 6 assigned to the sound source 4 is transparent to the used sound waves and produces an acoustical signal, which is used as a marking which is inserted in a predetermined manner, for example, as a light spot or a graticule, into the sonically generated image of the concrement 3. This light spot or graticule shows the position of the therapy focus of the therapy device.

For this purpose, the sensor 6, whose dimension advantageously corresponds to the diameter of the transmitter (scanner) of the emitted sound waves, consists of a plurality of individual elements which are designed such that, after a, for example, electrically adjustable time period which corresponds to the travel time of the sound to the location of the therapy focus and back, a signal is generated by the sensor. This signal is injected by the sensor into the signal trace of the imaging sound signal. In the sonic image, this signal is then visible as a reflection from an arbitrarily selected depth and location. By appropriate selection of the signal pattern, this reflection may be formed, for example, as a cross-hair in the sonically generated image at any point without electric intervention into the circuits of the sound source.

It is clear that, as a result, any sound scanners can be used in connection with the sensor according to the invention for producing a marking, because no special adaptation of the marking arrangement to the used sound source is necessary.

Figure 2:
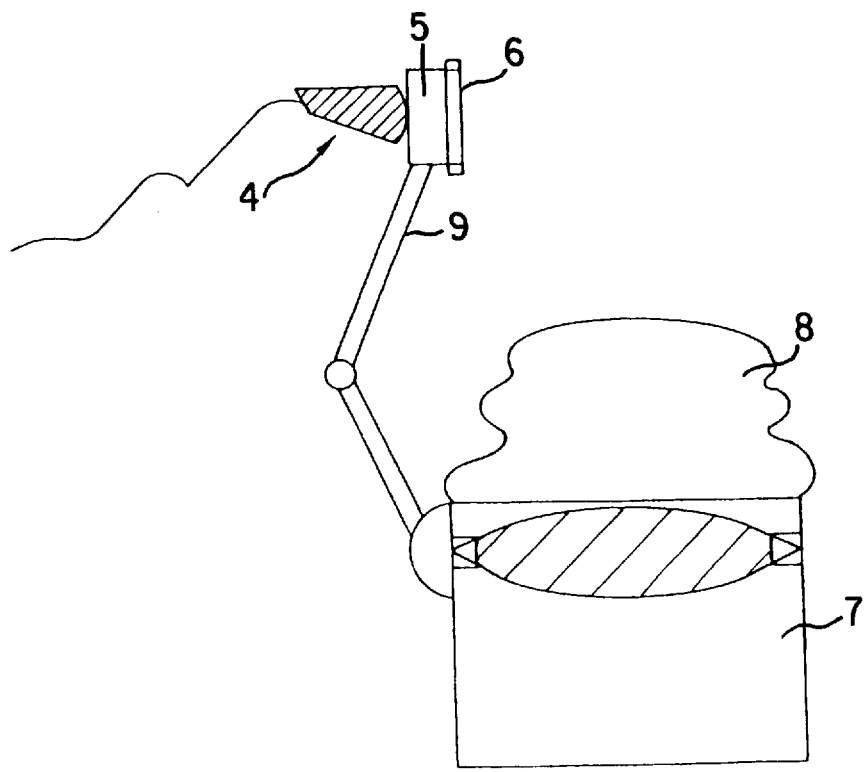
FIG. 2 is a sectional view of a part of the locating arrangement and of the therapy head.

FIG. 2 shows an arrangement in which the sensor 6 with the associated coupling arrangement is fastened on a holding device 9 which, in turn, is connected with a therapy head 7 of a shock wave generator. The latter is connected with the patient's body by way of a separate coupling arrangement 8. The holding device 9 permits a fixed positioning of the sensor 6 relative to the therapy head 7. Here also, the sensor 6 is designed such that, after the impinging of the locating sonic pulse emitted by the sound source 4 and after the expiration of a predetermined delay time, a signal is emitted by the sensor 6 which corresponds to twice the travel time of the sound to a therapy focus which is located at a designated predeterminable distance in the patient's body. This signal is imaged by the arrangement for representing the sonic image as a reflection from this predetermined depth.

By means of a corresponding design of the surface and the construction of the sensor 6 as an array or a mechanical forming-out, and by using the appropriate signals and time delays for the marking sonic pulses, any type of marking (for example, a graticule, a point or a circle) can be achieved at any location of the sound image.

Figure 3:
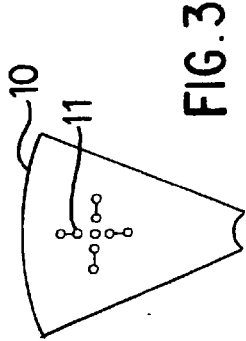
FIG. 3 is a view of a marking injected into a sonic image.

FIG. 3 is a schematic view of the sonic image 10 generated by the arrangement for representing the sound, with a, for example, acoustically injected graticule 11 which was generated by the sensor 6.

Figure 4:
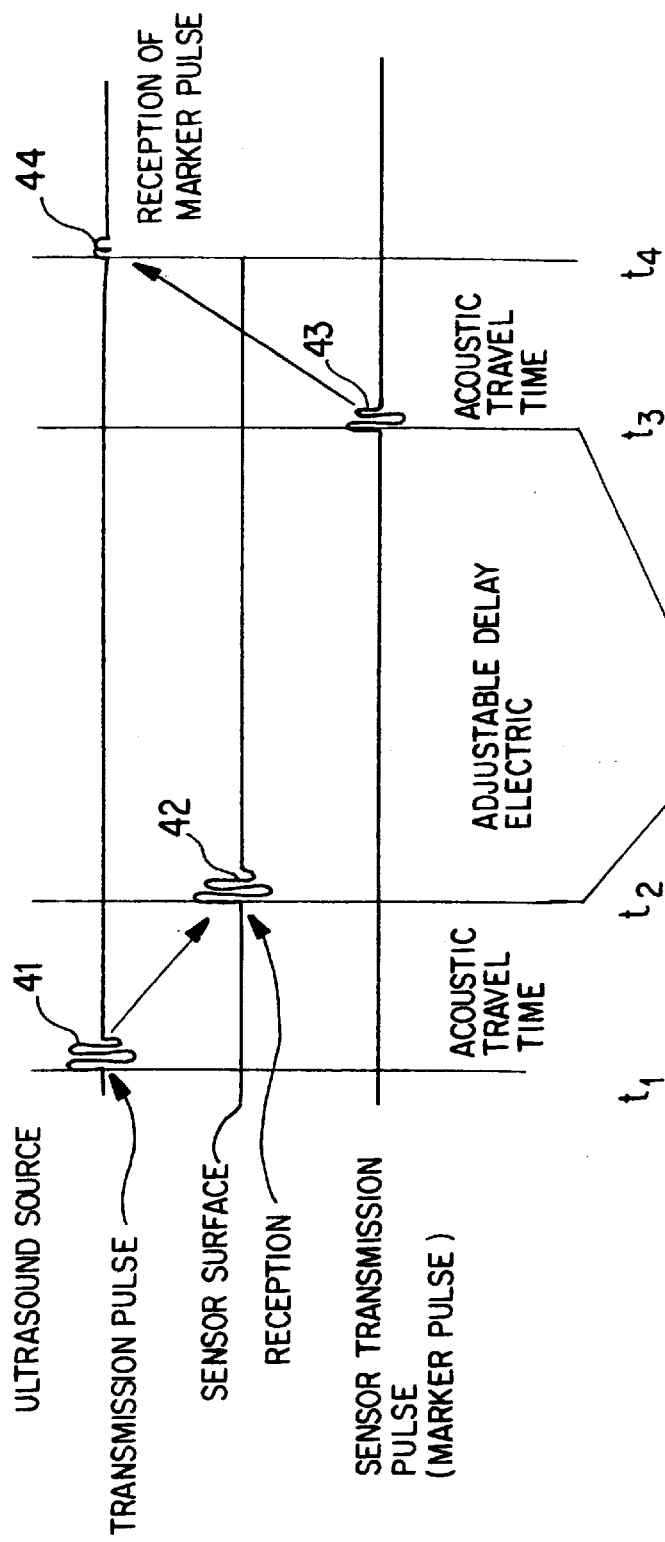
FIG. 4 is a diagram of a possible suitable pulse sequence.

FIG. 4 illustrates a diagram of a possible pulse sequence which shows the propagation of a pulse 41 generated by the sound source 4 at time $t_1$. This transmission pulse passes through the sensor 6 at time $t_2$, in response to which the sensor generates a signal 42. Thereafter the pulse travels through the patient's body, where it is reflected and returned through the sensor to the sound source. The sensor generates a marker pulse 43 at an adjustable time $t_3$. After the expiration of a, for example, electrically adjustable delay time ($t_3$-$t_2$), the sensor generates an output signal which is represented as a marking pulse in sonic image 10 when it is received at the time $t_4$.

These signals emitted by the sensor may be emitted in a location-selective manner; that is, they are generated only when one or several scanning lines of the sound source are detected. However, they can also be modified with respect to their form or their frequency content such that they generate a color-coded echo, for example, on a Doppler apparatus, which echo will then be represented as a marking in the sonic image.

The sensor 6 can be connected either directly with the sound source, for example, by way of the coupling arrangement 5, as illustrated in FIG. 1, or it can be connected by means of the mechanical holding device 9 on the therapy head of a lithotriptor or another therapy apparatus with a firm assignment to its focus. Finally, it is also possible to use the sensor 6 independently of the sound source 4 and the therapy head 7 only manually. In this case, corresponding distance sensors are used, for example, for the adjustable delay of the sensor in order to mark the position of the therapy focus in the sonic image 10, independently of the used therapy sound source.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. An apparatus for assisting in locating concrements in a patient's body, comprising:

a sound source for transmitting sound pulses;

a coupling device adapted to be placed between the sound source and the patient for introducing the generated sound pulses into the patient's body; and a second device for producing a marking; wherein the second device for producing the marking comprises a sensor which is transparent with respect to transmitted sound pulses when placed in a sound propagation path between the sound source and the patient;

the second device further includes means for generating a signal which is injected into a generated sonic image as a marking at an arbitrarily selectible point; and said generating means generates said signal after expiration of an adjustable delay time, following penetration of the second device by a sound pulse transmitted from said second device.

2. An apparatus according to claim 1, wherein the adjustable delay time corresponds to twice a travel time of a sound pulse between the sensor and a selectible depth in the patient's body.

3. An apparatus according to claim 1, wherein the sensor surface corresponds to a cross-sectional surface of the sound source.

4. An apparatus according to claim 1, wherein the sensor is composed of individual elements, whereby the generated signal has a predetermined form to provide a predetermined marking in the generated sonic image of the sound source.

5. An apparatus according to claim 1, wherein the sensor is arranged directly on the sound source.

6. An apparatus according to claim 1, wherein the sensor is removably attached to a therapy head by a mechanical holding device.

* * * * *